(12) United States Patent
Yang et al.

(10) Patent No.: US 10,716,941 B2
(45) Date of Patent: Jul. 21, 2020

(54) SYSTEM AND METHOD FOR CHARGE-BALANCING NEUROSTIMULATOR WITH NEURAL RECORDING

(71) Applicant: REGENTS OF THE UNVERSITY OF MINNESOTA, Minneapolis, MN (US)

(72) Inventors: Zhi Yang, Minneapolis, MN (US); Anh Tuan Nguyen, Minneapolis, MN (US); Jian Xu, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 194 days.

(21) Appl. No.: 15/864,668

(22) Filed: Jan. 8, 2018

(65) Prior Publication Data
US 2018/0193647 A1  Jul. 12, 2018

Related U.S. Application Data

(60) Provisional application No. 62/443,503, filed on Jan. 6, 2017.

(51) Int. Cl.
*A61N 1/36* (2006.01)
*A61N 1/02* (2006.01)
(Continued)

(52) U.S. Cl.
CPC ........ *A61N 1/36135* (2013.01); *A61B 5/0031* (2013.01); *A61B 5/04001* (2013.01);
(Continued)

(58) Field of Classification Search
CPC ........ A61N 1/025; A61N 1/0551; A61N 1/08; A61N 1/36; A61N 1/36125;
(Continued)

(56) References Cited

U.S. PATENT DOCUMENTS

| | | | |
|---|---|---|---|
| 2007/0016263 A1* | 1/2007 | Armstrong | A61N 1/0551 607/45 |
| 2007/0142874 A1* | 6/2007 | John | A61N 1/3605 607/45 |

(Continued)

OTHER PUBLICATIONS

Lee et al. "A Power-Efficient Switched-Capacitor Stimulating System for Electrical/Optical Deep Brain Stimulation," in IEEE Journal of Solid-State Circuits, vol. 50, No. 1, pp. 360-374, Jan. 2015.

(Continued)

*Primary Examiner* — Christopher A Flory
(74) *Attorney, Agent, or Firm* — Quarles & Brady LLP

(57) ABSTRACT

Systems and methods are provided for an implantable neurostimulator system comprising an array of microelectrodes, a pair of current drivers, and a dynamic current allocation network (DCAN). Each current driver in the pair of current drivers is configured to deliver a respective portion of an electrical signal to the array of microelectrodes to deliver the desired electrical stimulation through the array of microelectrodes to the subject. The DCAN is coupled to the pair of current drivers and the array of microelectrodes to selectively electrically connect each of the pair of the current drivers to individual microelectrodes in the array of microelectrodes to deliver the electrical signal to selective collections of less than all microelectrodes in the array of microelectrodes to deliver the desired electrical stimulation. The pair of current drivers and the DCAN are arranged in respective or a common housing configured to be implanted into the subject.

20 Claims, 17 Drawing Sheets

(51) Int. Cl.
*A61N 1/05* (2006.01)
*A61B 5/00* (2006.01)
*A61N 1/372* (2006.01)
*A61B 5/04* (2006.01)
*A61N 1/08* (2006.01)
*A61B 5/1495* (2006.01)

(52) U.S. Cl.
CPC .......... *A61B 5/1495* (2013.01); *A61B 5/4064* (2013.01); *A61B 5/4088* (2013.01); *A61B 5/4836* (2013.01); *A61B 5/6868* (2013.01); *A61N 1/025* (2013.01); *A61N 1/0551* (2013.01); *A61N 1/08* (2013.01); *A61N 1/36125* (2013.01); *A61N 1/37205* (2013.01); *A61B 2562/046* (2013.01)

(58) Field of Classification Search
CPC ............ A61N 1/36135; A61N 1/37205; A61B 5/04001; A61B 5/4836
See application file for complete search history.

(56) References Cited

U.S. PATENT DOCUMENTS

| | | | | |
|---|---|---|---|---|
| 2010/0152817 | A1* | 6/2010 | Gillbe | A61N 1/0551 607/72 |
| 2010/0174341 | A1* | 7/2010 | Bolea | A61N 1/3601 607/42 |
| 2011/0125224 | A1* | 5/2011 | Carbunaru | A61N 1/36071 607/66 |
| 2011/0160794 | A1* | 6/2011 | Bolea | A61N 1/3601 607/42 |
| 2012/0192874 | A1* | 8/2012 | Bolea | A61N 1/3601 128/848 |
| 2013/0268025 | A1* | 10/2013 | Ranu | A61N 1/08 607/59 |
| 2014/0025715 | A1 | 1/2014 | Yang et al. | |
| 2014/0228905 | A1* | 8/2014 | Bolea | A61N 1/0556 607/42 |
| 2014/0371515 | A1* | 12/2014 | John | A61N 2/02 600/13 |
| 2015/0174417 | A1* | 6/2015 | Ranu | A61N 1/08 607/59 |
| 2015/0223971 | A1* | 8/2015 | Zaveri | A61B 5/0478 607/113 |
| 2015/0226615 | A1* | 8/2015 | Feldman | G01K 13/002 374/185 |
| 2016/0008602 | A1* | 1/2016 | Perryman | H02J 50/20 607/61 |
| 2016/0089540 | A1* | 3/2016 | Bolea | A61N 1/36139 607/42 |
| 2016/0144183 | A1* | 5/2016 | Marnfeldt | A61N 1/36125 607/63 |
| 2016/0144184 | A1* | 5/2016 | Marnfeldt | A61N 1/36125 607/63 |
| 2017/0143969 | A1* | 5/2017 | Sarpeshkar | A61N 1/36125 |
| 2017/0189683 | A1* | 7/2017 | Perryman | H02J 50/20 |

OTHER PUBLICATIONS

Lo et al. "A Fully-Integrated High-Compliance Voltage SoC for Epi-Retinal and Neural Prostheses," in IEEE Transactions on Biomedical Circuits and Systems, vol. 7, No. 6, pp. 761-772, Dec. 2013.

Nag et al. "A 24 Vpp compliant biphasic stimulator for inductively powered animal behavior studies," 2013 35th Annual International Conference of the IEEE Engineering in Medicine and Biology Society (EMBC), Osaka, 2013, pp. 3242-3245.

Shulyzki et al. "256-site active neural probe and 64-channel responsive cortical stimulator," 2011 IEEE Custom Integrated Circuits Conference (CICC), San Jose, CA, 2011, pp. 1-4.

Williams et al. "An Energy-Efficient, Dynamic Voltage Scaling Neural Stimulator for a Proprioceptive Prosthesis," in IEEE Transactions on Biomedical Circuits and Systems, vol. 7, No. 2, pp. 129-139, Apr. 2013.

* cited by examiner

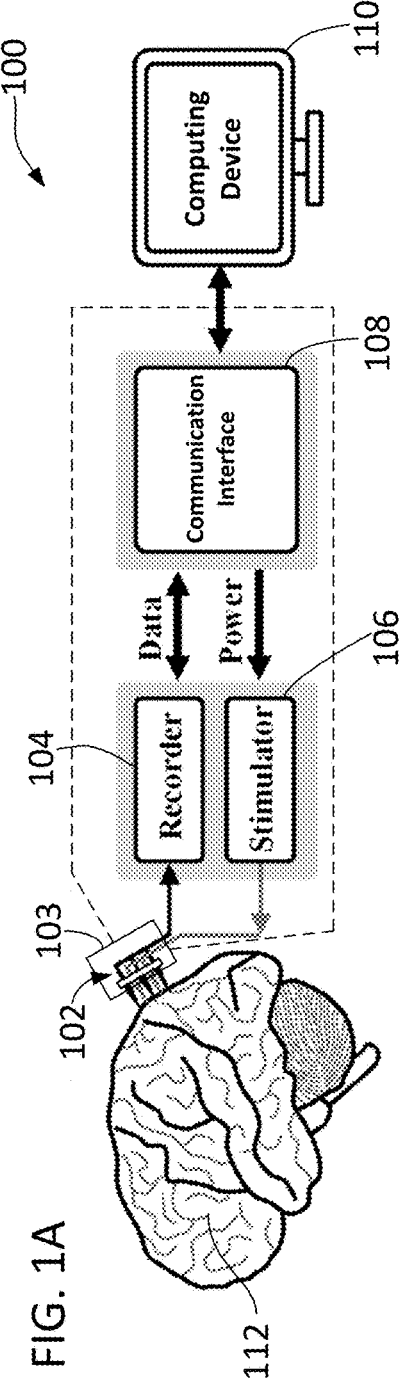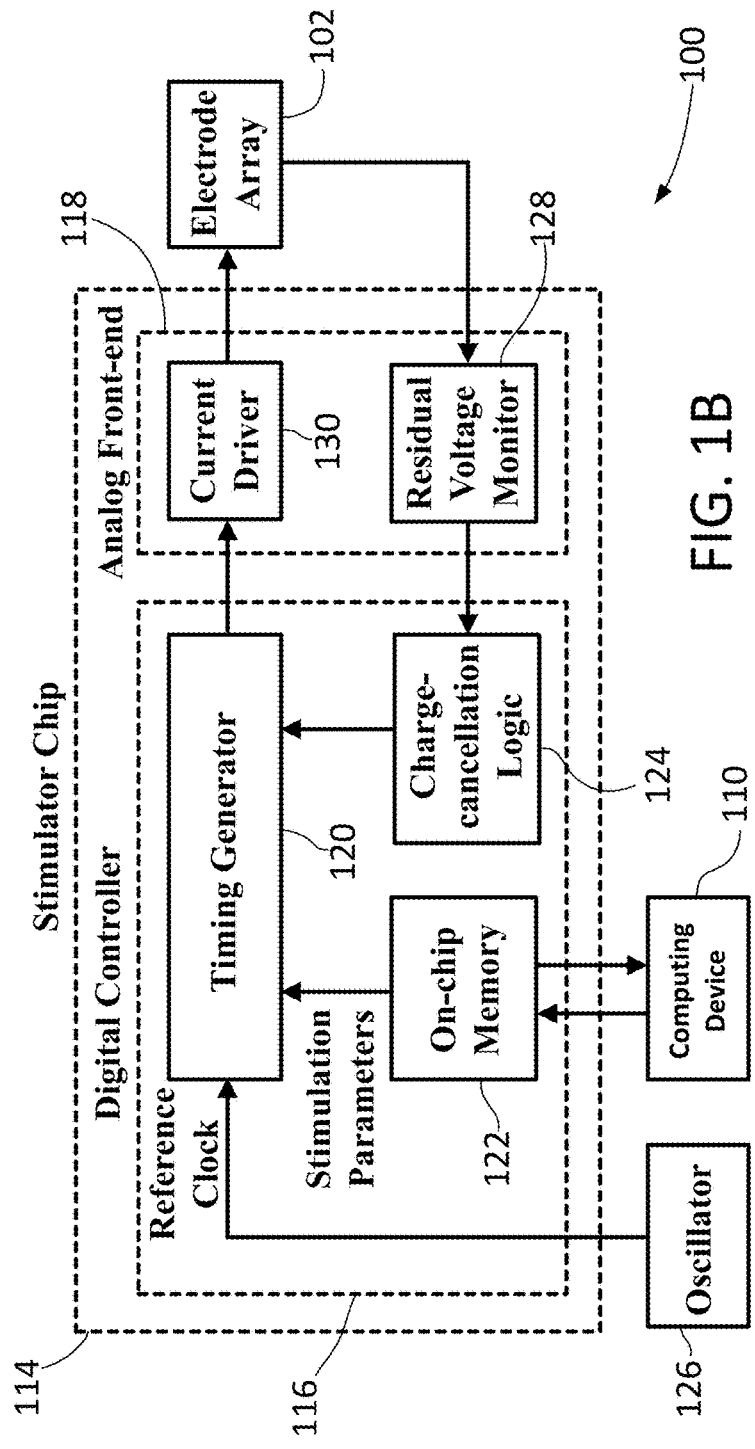
FIG. 1A
FIG. 1B

Symmetrical Biphasic

Asymmetrical Biphasic

Monophasic/Pulse Train

SYSTEM AND METHOD FOR CHARGE-BALANCING NEUROSTIMULATOR WITH NEURAL RECORDING

CROSS-REFERENCE TO RELATED APPLICATIONS

This application is based on, claims priority to, and incorporates herein by reference in its entirety for all purposes, U.S. Provisional Application Ser. No. 62/443,503, filed Jan. 6, 2017, and entitled, "SYSTEM AND METHOD FOR CHARGE-BALANCING NEUROSTIMULATOR WITH NEURAL RECORDING."

BACKGROUND

The present disclosure relates generally to systems and methods for neurostimulation and neural recording and, more particularly, to systems and methods for operating a microstimulator with charge-balancing techniques for biomedical implants and instrumentation.

The use of electrical microstimulation to manipulate neuronal circuits has been studied for many years. Techniques related to electrical microstimulation enable a wide variety of biomedical applications including neuroprosthetics to restore motor and sensory function, neurorepair to aid rehabilitation from brain injuries, and neurotherapeutics to treat nervous system disorders. A recent trend is to develop new technologies that can perform closed-loop microstimulation at a large-scale. There are multiple challenges to obtaining neuro-feedback while stimulating, and work continues on lessening residual voltage and stimulation artifacts.

Conventional stimulator designs use discrete components to achieve high-voltage compliance and high output impedance. However, such stimulators, which are bulky, have low-channel-count, and have high power consumption, are not suitable for implantable devices. Custom system-on-chip (SoC) stimulators often employ a feedback-assisted current mirror structure and high voltage process. However, these systems present a large chip area that is undesirable for implantation. Some systems use off-chip DC blocking capacitors instead of efficient charge-balancing mechanisms. As a result, these systems often have poor channel density and are difficult to be integrated into large-scale stimulator implants.

Prior high-channel stimulator SoCs with tens to hundreds of channels trade off channel density for performance by using a simple cascode current mirror structure, which cannot offer sufficient output impedance. They also lack mechanisms to actively monitor residual charge and ensure charge-balancing in favor of increasing channel count. These stimulators are not suitable for acute microstimulation applications, such as (for example) cortical stimulation and vagus nerve stimulation.

Thus, there is a need for new and refined systems, methods, and architectures for implantable neurostimulators.

SUMMARY

The present disclosure provides systems and methods that overcome the aforementioned drawbacks using an integrated, high-voltage, high-density microstimulator with charge-balancing techniques for biomedical implants and instrumentation.

In accordance with one aspect of the present disclosure, systems and methods are provided for an implantable neurostimulator system comprising an array of microelectrodes, a pair of current drivers, and a dynamic current allocation network (DCAN). The array of microelectrodes is configured to deliver a desired electrical stimulation to a subject. The pair of current drivers is electrically coupled to each microelectrode in the microelectrode array. Each current driver in the pair of current drivers is configured to deliver a respective portion of an electrical signal to the array of microelectrodes whereby the respective portions, together, form the electrical signal delivered to the array of microelectrodes to deliver the desired electrical stimulation through the array of microelectrodes to the subject. The dynamic current allocation network is coupled to the pair of current drivers and the array of microelectrodes to selectively electrically connect each of the pair of the current drivers to individual microelectrodes in the array of microelectrodes to deliver the electrical signal to selective collections of less than all microelectrodes in the array of microelectrodes to deliver the desired electrical stimulation. The pair of current drivers and the DCAN are arranged in respective or a common housing configured to be implanted into the subject.

In accordance with another aspect of the present disclosure an implantable neurostimulator system comprises an array of microelectrodes, a pair of current drivers, a dynamic current allocation network (DCAN), and a controller. The array of microelectrodes is configured to deliver a desired electrical stimulation to a subject. The pair of current drivers is electrically coupled to each microelectrode in the microelectrode array. Each current driver in the pair of current drivers is configured to deliver a respective portion of an electrical signal to the array of microelectrodes whereby the respective portions, together, form the electrical signal delivered to the array of microelectrodes to deliver the desired electrical stimulation through the array of microelectrodes to the subject. The DCAN is coupled to the pair of current drivers and the array of microelectrodes to selectively electrically connect each of the pair of the current drivers to individual microelectrodes in the array of microelectrodes to deliver the electrical signal to selective collections of less than all microelectrodes in the array of microelectrodes to deliver the desired electrical stimulation. The controller is configured to control the DCAN to selectively electrically connect each of the pair of the current drivers to individual microelectrodes in the array of microelectrodes to cause the desired electrical stimulation delivered to the subject match a stored waveform.

Further advantages and features of the invention will be apparent from the remainder of this document in conjunction with the associated drawings.

BRIEF DESCRIPTION OF THE DRAWINGS

FIG. 1A provides an illustration of a system that combines electrical microstimulation and recording in accordance with the present disclosure.

FIG. 1B provides an exemplary simplified block diagram of a microstimulator chip in the system of FIG. 1A.

DETAILED DESCRIPTION

Figure 2:
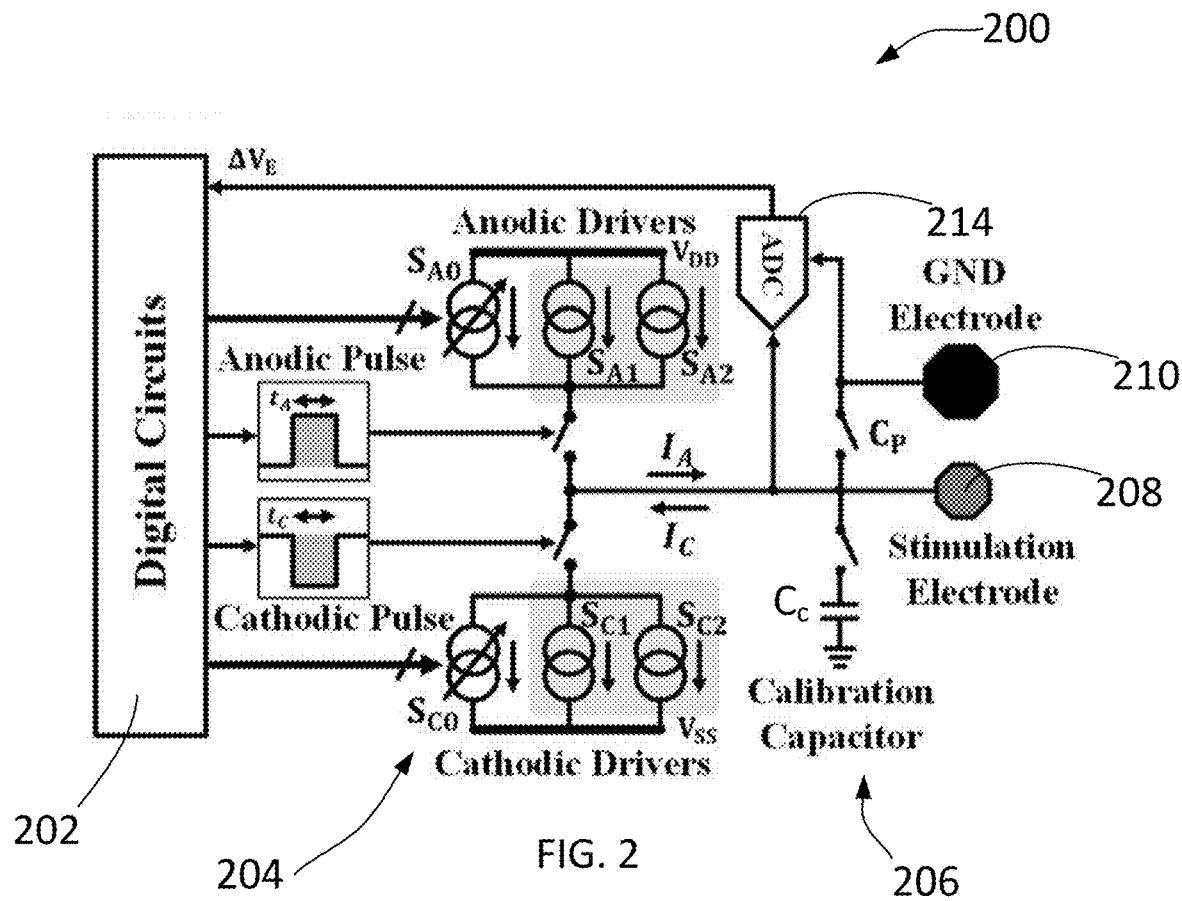
FIG. 2 is an exemplary simplified block diagram of one stimulation channel in the system of FIG. 1A.

Exemplary systems and methods provide a high-voltage, integrated neural stimulator chip that features enhanced charge-balanced characteristics and high channel density. In one configuration, the design may be based on a feedback-assisted current allocation network and implemented in a high-voltage CMOS process that delivers very high output impedance (3.6 T$\Omega$@8 µA for anodic current driver and 82.3 T$\Omega$@-8 µA for cathodic current driver) and output voltage compliance (up to 19V at a 20V power supply).

Complementary charge-balancing techniques may be integrated to reduce residual voltage and stimulation artifacts. Such techniques can include a foreground calibration and a background active charge-balancing mechanism. An active charge-balancing scheme also reduces or removes the need for external DC blocking capacitors, thus making the stimulator suitable for high-channel implantable devices. The design can be used to achieve a desirable trade-off between high-performance (high-voltage, high output impedance, charge-balancing, etc.) and channel density due to adequate resource sharing and efficient chip layout. The design can be scaled to materialize fully-integrated, implantable devices with (for example) hundreds-to-thousands of stimulation channels on a millimeter-size chip die.

In some exemplary versions, the design features a basic feedback-assisted structure and resource sharing strategy. In other configurations, each pair of current drivers can be employed with a dynamic current allocation network (DCAN) that allows one set of drivers to support multiple non-concurrent stimulation channels. In some ways, the DCAN serves the function of a current steering network, but as will be described, the DCAN is designed to use multiple current drivers/generators such that (i) one channel can support multiple electrodes through interleaved high-frequency stimulation, (ii) each electrode can be driven by multiple channels, and (iii) several channels can be combined to drive an electrode for a higher current limit. In the proposed circuits, the assignment of driver/generator to electrode(s) is dynamically computed based on the number of electrodes and output demand, where the scheduling algorithm has been implemented and integrated into the chip. This allows the stimulator to be configured to match the specifications of different applications. For example, brain stimulation using microelectrode array has many electrodes with low current limit, while nerve stimulation using cuff electrode have fewer channels but require a high current limit.

One of the output terminals can be connected to an external capacitor to perform foreground current calibration. A single external capacitor can be shared among all channels of the microsystem. Moreover, a low-resolution successive-approximation register (SAR) analog-to-digital converter (ADC) can be used in conjunction with or in place of the comparator for monitoring the residual voltage. The SAR ADC may also be shared among multiple channels.

The system may be adapted to a fully-integrated stimulator chip for electrical microstimulation that provides many advantages. The device may be designed in a high voltage process that allows up to 20V power supply and 19V output voltage compliance. A broad range of current-mode stimulation waveforms and patterns can be generated, including symmetrical/asymmetrical, biphasic/monophasic, and pulse train stimuli. The current amplitude, pulse width, and stimulation rate are preferably adjustable from 0.5 µA to 2 mA, 100 µs to 4 ms, and 0.1 Hz to 200 Hz, respectively. Two complementary charge-balancing techniques may be integrated to reduce residual voltage and stimulation artifacts. In in vitro experiments, the stimulator was used to trigger neural spikes, modulate neuronal firing rate, and alter mesoscopic neuronal activity. The microstimulator can support a wide variety of neuroscience applications and experiments requiring electrical microstimulation.

Regarding overall system architecture, FIG. 1A provides one non-limiting example of a microsystem 100 for closed-loop neural stimulation. The microsystem 100 includes a microelectrode array 102, a recorder 104, a stimulator 106, a customized communication interface 108 (e.g., a universal serial bus—USB communication interface), and a computing device 110. As illustrated, the microelectrode array 102 is engaged with a brain 112 of a subject (not shown). In other instances, the microelectrode array 102 can be attached to other tissues or organic structures, for example, muscle tissue, epidural tissue or matter, or any other material or tissue desired for stimulation. The microelectrode array 102 may be arranged partially within a housing 103. The housing 103 may additionally envelop the recorder 104, the stimulator 106, and the communication interface 108. The stimulation waveforms, patterns, and parameters may be programmed through suitable wired or wireless communications interface 108 (such as USB) that may connect to the computing device 110, which may be a computer, portable tablet or phone, or other computing device. Operation of the microsystem 100 may be controlled by an internal clock generator after the initial configuration, such as will be described.

Referring now to FIG. 1B, in some instances, the recorder 104, the stimulator 106, and the communication interface 108 of the microsystem 100 can be included on a stimulator microchip 114, which may be disposed within the housing 103. The stimulator microchip 114 contains a digital controller 116 and an analog front-end 118. The digital controller 116 includes a timing generator 120, an on-chip memory 122, and a charge cancellation logic 124. The timing generator 120 is in communication with an oscillator 126 or an internal clock (not shown) to guide system operation. The on-chip memory 122 is in communication with the computing device 110 and the timing generator 120. The charge-cancellation logic 124 is in communication with the timing generator 120 and a residual voltage monitor (RVM) 128 of the analog front-end 118.

In some instances, the analog front-end 118 includes a current driver 130 and the residual voltage monitor 128. The current driver 130 can receive stimulation patterns and stimulation timing for the electrodes in the electrode array 102 from the timing generator 120. Once the current driver 130 has stimulated the electrodes, the residual voltage monitor 128 can receive stimulation signals from the electrode array 102. The residual voltage monitor 128 can then determine an amount of residual voltage or charge built up within the electrode array 102, and can communicate the residual voltage or charge through the charge-cancellation logic 124 to the timing generator 120 to minimize the residual voltage or charge built up within the electrode array during stimulation.

As such, a user can input the desired stimulation parameters (e.g., amplitude, frequency, duty cycle, stimulation patterns, stimulation timings, etc.) for each electrode in the microelectrode array 102 using a stimulation waveform programming unit, such as the computing device 110. The computing device 110 can then calculate the best switching and mixing combination to match the stimulation patterns and timings with the desired ones. Then, once the stimulation parameters are determined, they can be sent to the on-chip memory 122 of the digital controller 116, which can automatically generate the necessary stimuli based on the pre-programmed set of parameters, thereby reducing the data transmission between the chip 114 and the computing device 110. Additionally, the on-chip residual voltage monitor 128 and charge cancellation logic 124 allow for faster adaptation of the stimulation patterns.

FIG. 2 shows the simplified diagram 200 of one stimulation channel that, as a non-limiting example, illustrates three functional blocks: digital circuits 202, current drivers 204, and charge-balancing circuits 206. The digital circuits 202 can be configured to apply stimulation parameters to the current drivers 204. Each current driver can include two matched sub-drivers, namely ($S_{A1}$, $S_{A2}$) and ($S_{C1}$, $S_{C2}$), which can be independently controlled to deliver flexible stimulation waveforms to the stimulation electrode 208.

Figure 4:
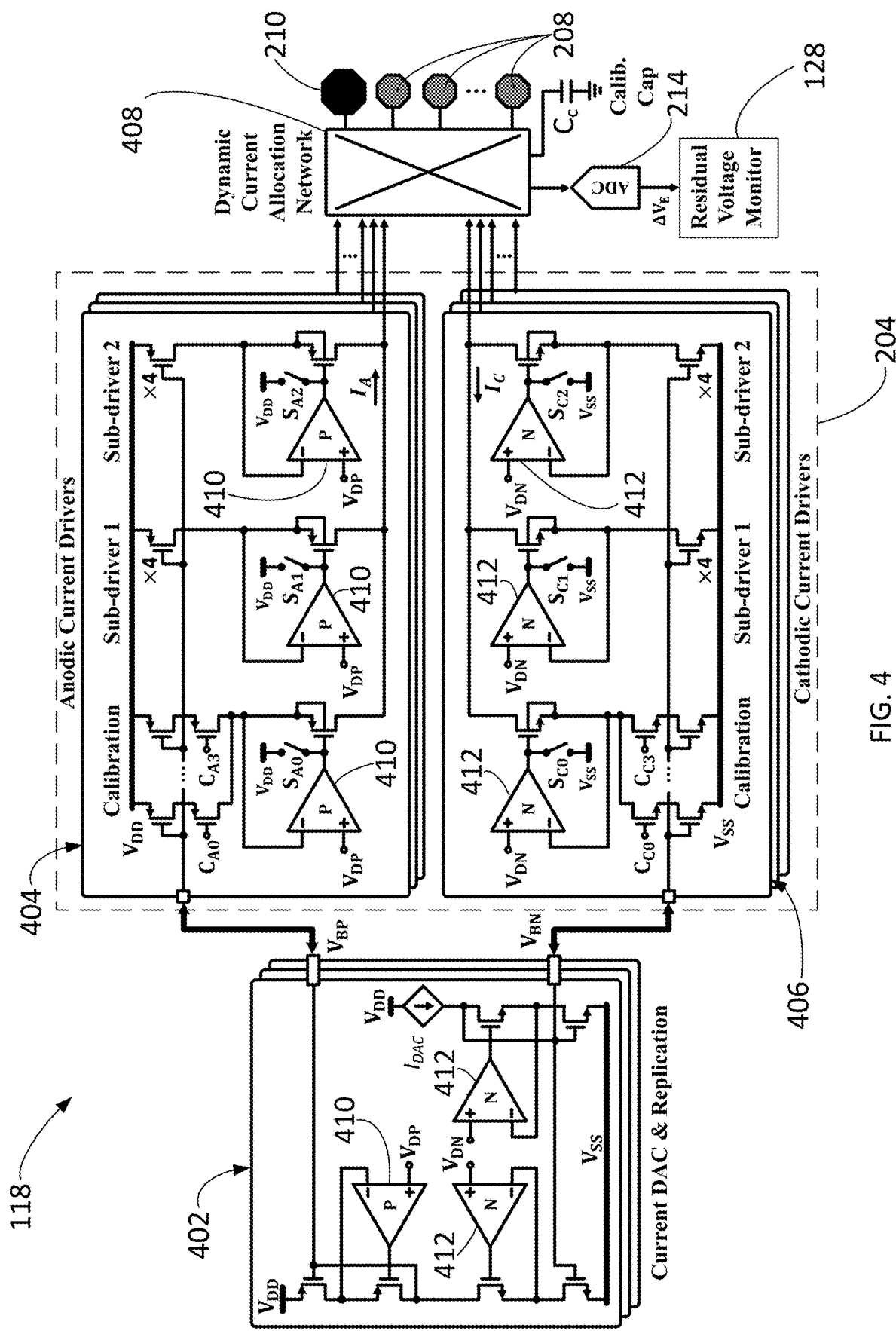
FIG. 4 is a circuit diagram that provides circuit schematics for a microstimulator in accordance with the present disclosure.

Regarding circuit implementations, FIG. 4 provides one, non-limiting example of the analog front-end 118 of the stimulator chip 114 described above. The analog front-end 118 can include several primary blocks: the current digital-to-analog converter (IDAC) and current replication circuits (CRC) block 402, a first set of current drivers 404, a second set of current drivers 406, a dynamic current allocation network (DCAN) 408, and the residual voltage monitor 128. As will be described, the first and second set of current drivers 404, 406 are designed to deliver complementary, or reciprocal, coordinated performance. In this way and in a non-limiting manner other than to connote the complementary performance, the first and second current drivers may be referred to as anodic current drivers 404 and cathodic current drivers 406.

As such, the pair of current drivers 404, 406 are electrically coupled to each microelectrode in the microelectrode array and each current driver 404, 406 in the pair of current drivers 404, 406 is configured to deliver a respective portion of an electrical signal to the array of microelectrodes whereby the respective portions, together, form the electrical signal delivered to the array of microelectrodes 208 to deliver the desired electrical stimulation through the array of microelectrodes 208 to the subject. The analog front-end 118 can further include a plurality of "P" amplifiers 410 and "N" amplifiers 412 adopted for impedance boosting, as will be described below.

Notably, as will be described, the DCAN 408 provides capabilities and functionality not available in prior-art systems that rely on, for example, current steering systems. For example, some traditional stimulators use current steering to stimulate at multiple electrodes at the same time with a specific geometrical configuration of the electrode array to generate a compound electrical field distribution to stimulate neural tissue. In this way, such "current steering" systems "steer" the electrical current in 3-D extracellular space to achieve some selectivity in stimulation. In other systems, so-called "current steering digital-to-analog converters (DAC)" have been used to generate an internal reference voltage for circuit operation. As such, "current steering" in this context is a classic technique that has been widely used in modern digital-to-analog converter (DAC) designs.

On the other hand, the systems and methods of the present disclosure use multiple current drivers/generators to drive one or more electrodes concurrently or use one current driver/generator to support multiple electrodes simultaneously through interleaved high-frequency stimulation. Thus, the systems and methods provided herein use the DCAN 408, which is coupled to the current drivers 404, 406 and the array of microelectrodes 208, to control the assignment of driver/generator to electrode(s) dynamically based on the number of electrodes and output demand. The scheduling algorithm can be implemented and integrated into the DCAN 408. In this way, operation of the DCAN 408 can execute several tasks in parallel. As such, when the stimulation demand is low, several pairs of drivers 404, 406 can stimulate one stimulation electrode 208 in parallel to accelerate the stimulation; when the stimulation demand is high, one pair of drivers 404, 406 can support several stimulation electrodes 208 concurrently via time-interleaving.

Together, the IDAC and CRC 402 converts the output ($I_{DAC}$) of the IDAC to a biasing voltage for anodic drivers 404 ($V_{BP}$) and cathodic drivers 406 ($V_{BN}$). $V_{BP}$ and $V_{BN}$ are then converted into stimulation output ($I_A$ and $I_C$) by the corresponding current drivers. The IDAC and CRC 402 can be shared by several anodic/cathodic current drivers 404, 406 to reduce the chip area.

The current drivers 404, 406 are designed based on a feedback-assisted current mirror structure that allows achieving ultra-high output impedance (in the order of GΩ to TΩ). The ultra-high output impedance enables charged delivered and residual charge to be less dependent on the type of electrodes. As illustrated in FIG. 4, to deliver both symmetrical and asymmetrical biphasic stimuli, each driver can have two identical but independently programmable sub-drivers (Sub-driver 1 and Sub-driver 2), each with a×4 current multiplier. Each driver can also include a calibration sub-driver (Calibration) with a×0.05 multiplier and 4-bit resolution adjustability to fine-tune the output current. Overall, the current output from each driver 404, 406 ($I_A$ and $I_C$) is given as follows:

$$I_A \text{ or } I_C = I_{DAC} \cdot (4S_0 + 4S_1 + 0.05 S_C)$$

$$I_{DAC} = x_D \cdot I_{ref}$$

where $S_0, S_1 \in \{0, 1\}$ are the digital codes for the two sub-drivers, $S_C \in \{0, 1, \ldots, 15\}$ is the 4-bit digital code for the calibration sub-driver, $I_{DAC}$ is the output of the IDAC, $x_D \in \{0, 1, \ldots, 255\}$ is the 8-bit digital code for the IDAC, $I_{ref}$ is a reference current that is shared among the entire chip. $I_{ref}$ can be configured to 0.5 µA deliver low current stimuli or 4 µA to deliver high current stimuli. This allows the stimulator to generate a broad range of output current from 0.5 µA to 2 mA.

The output current ($I_A$ and $I_C$) of the drivers 404, 046 are fed into the DCAN 408. The DCAN 408 can arbitrarily route the output from one driver to any stimulation electrode 208 based on the current demand. As a result, (i) one driver can support multiple electrodes, (ii) each electrode can be driven by multiple drivers, and (iii) several drivers can be combined to drive an electrode for a higher current limit. The switching operation of the DCAN 408 can be governed by the digital controller 116 and be transparent to the end-user. The DCAN 408 can also allow several secondary functions. For example, each stimulation electrode 208 can be shorted to the GND electrode 210 for passive discharging. Also, each stimulation electrode 208 can also be connected to the RVM for background charge-cancellation. Further, the output from any driver 204 can be routed to a calibration capacitor for foreground calibration.

Figure 5C:
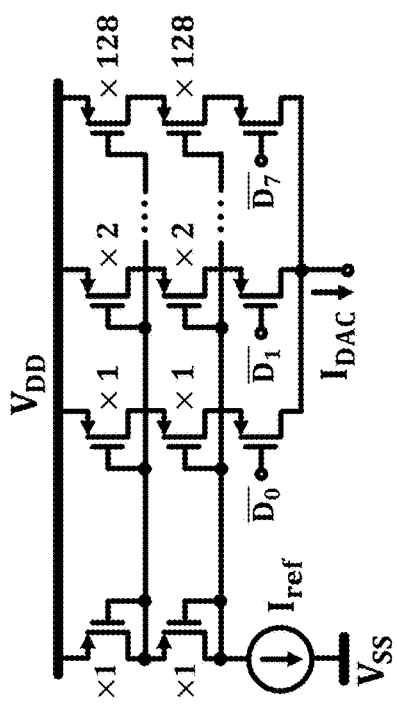
FIG. 5C is a circuit diagram that provides circuit schematics for a current digital-to-analog converter (IDAC) that adopts a two-stage cascade design and has an 8-bit resolution for use in the systems of the present disclosure.
Figure 5D:
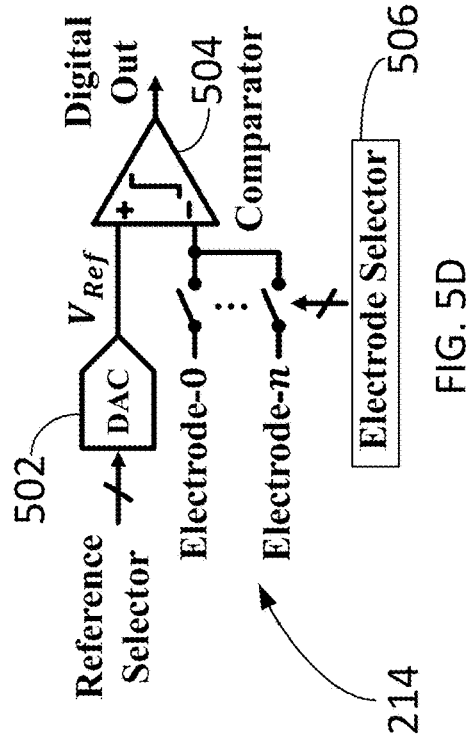
FIG. 5D is a circuit diagram that provides an equivalent low-resolution successive-approximation register (SAR) analog-to-digital converter (ADC) used to monitor residual voltage (a comparator is equivalent to 1-bit SAR ADC) for use in the systems of the present disclosure.
Figure 5B:
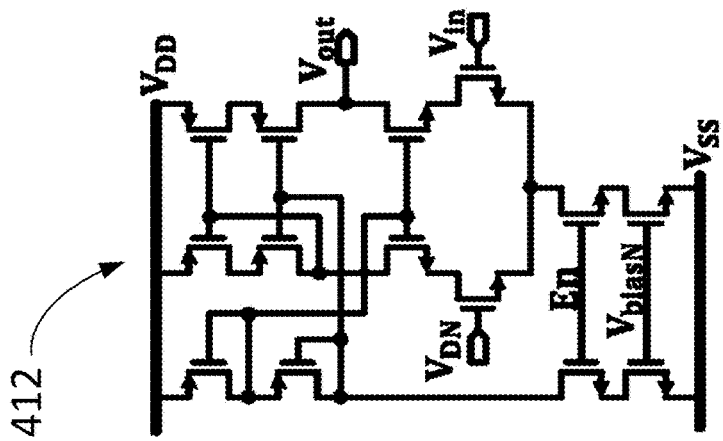
FIG. 5B is a circuit diagram that provides circuit schematics for an N-type amplifier for use in the systems of the present disclosure.
Figure 5A:
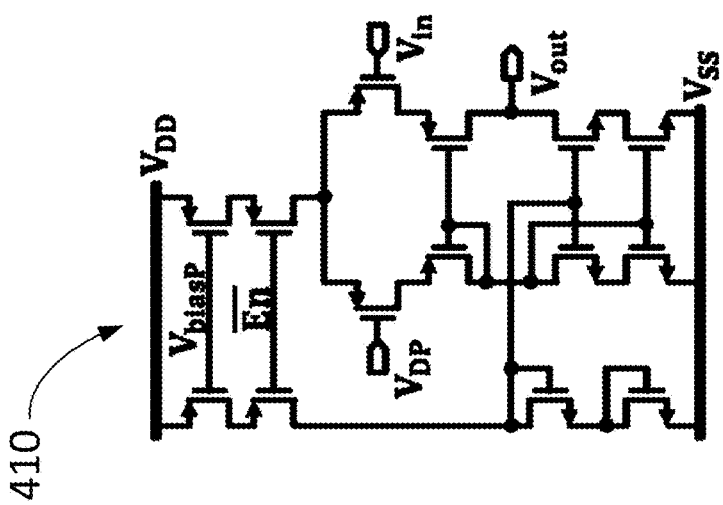
FIG. 5A is a circuit diagram that provides circuit schematics for a P-type amplifier for use in the systems of the present disclosure.

FIGS. 5A and 5B show schematics of the two different amplifier implementations described for impedance boosting as shown in FIG. 4. The "P" amplifier 410 (shown in FIG. 5A) is designed to work with an input DC-bias voltage $V_{DP}$ which is close to $V_{DD}$, while the "N" amplifier 412 (shown in FIG. 5B) is designed with opposite biasing conditions. Both implantations are based on the single-stage cascode design to achieve fast settling time while still providing adequate input/output range. To reduce static power consumption, the bias current of each amplifier can be shut down during inter-stimulus intervals. FIG. 5C shows a schematic of the IDAC that adopts a two-stage cascode design and has an 8-bit resolution.

FIG. 5D shows the schematic of the low-resolution SAR ADC 214 for the RVM 128, which can include a digital-to-analog converter 502 to generate a reference voltage ($V_{ref}$), a comparator 504, and an electrode selector 506 that is part of the DCAN 408. The SAR ADC 214 can be a one-channel high-voltage ADC shared between multiple electrodes.

Figure 6A:
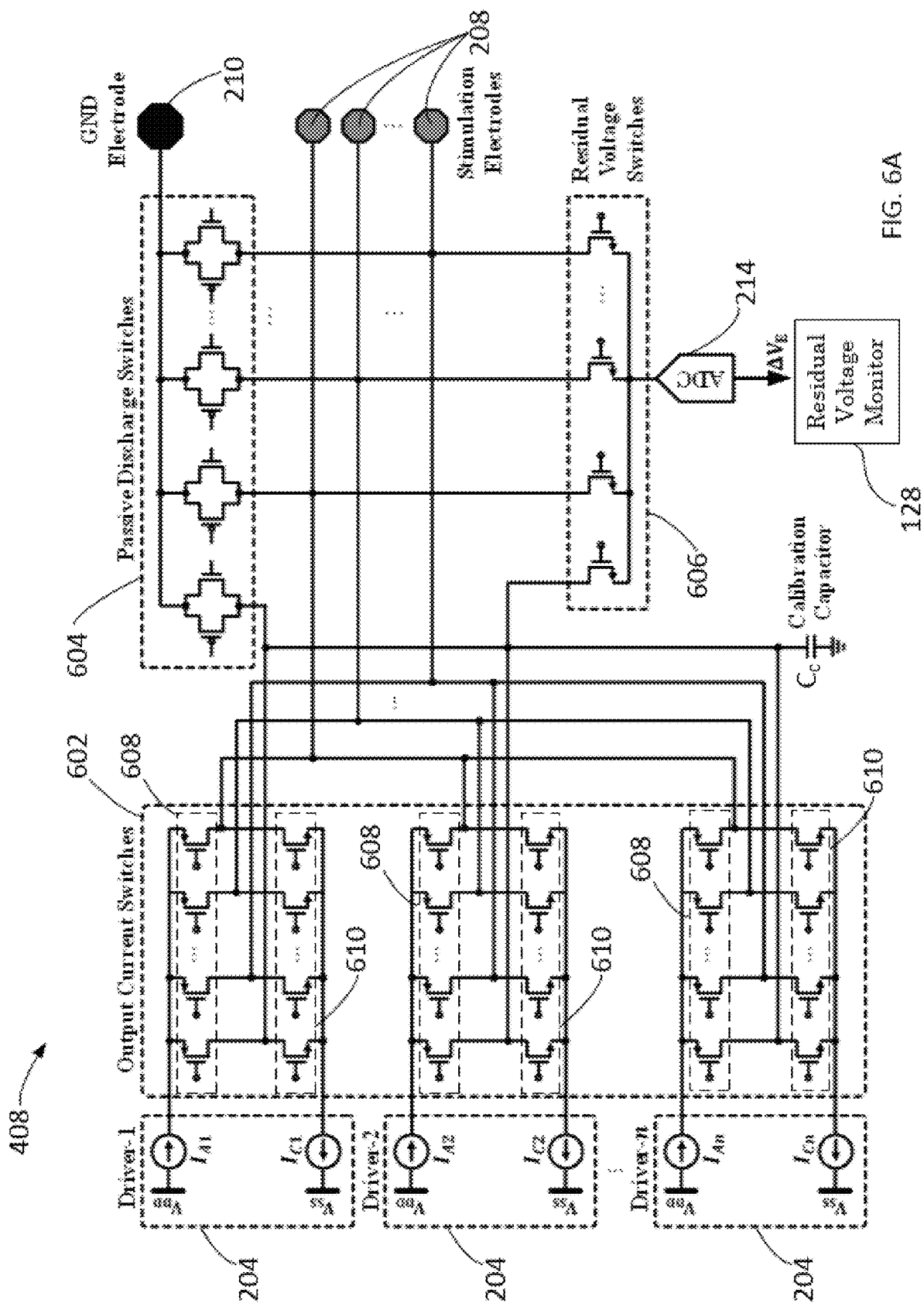
FIG. 6A is a circuit diagram that provides circuit schematics for a dynamic current allocation network (DCAN) for use in the systems of the present disclosure.

FIG. 6A shows the schematic of the DCAN 408 that includes three sets of switches: the output current switches 602, the passive discharge switches 604, and the residual voltage switches 606. The output current switches 602 each have a complimentary pair of a PMOS 608 and an NMOS 610, which allow routing the output of any current driver to an arbitrary stimulation electrode 208 or the calibration capacitor $C_c$. The passive discharge switches 604 allow shorting any stimulation electrode 208 to a GND electrode 210. The residual voltage switches 606 allow connecting any stimulation electrode 208 or the calibration capacitor $C_c$ to the RVM 128.

At the circuits' level, the gates of all bias transistors in the current driver 204 are driven by the output of corresponding op-amps, which provide much faster settling time compared to a simple current mirror or cascode current mirror. Second, the current switching action can be performed entirely with the DCAN 408, which can allow fast turning on/off for the output current. In FIG. 4, the current switching is done through controlling the gate voltage of the cascade transistors ($S_{C1}, S_{C2}, S_{A1}, S_{A2}$), thus having slower action.

As such, the disclosed stimulator chip 114 is much faster than those in the related literature. It can generate stimulation waveforms that have fast rising and falling edges (<1 µs) and reach a stimulation rate of 300 KHz. The DCAN, in combination with the capability to generate high-frequency waveforms, enables one-channel stimulator scanning through multiple electrodes at a higher speed and simultaneously deliver the stimuli through multiple electrodes. This allows reducing the size and cost of the stimulator while still support a large number of electrodes.

Figure 6B:
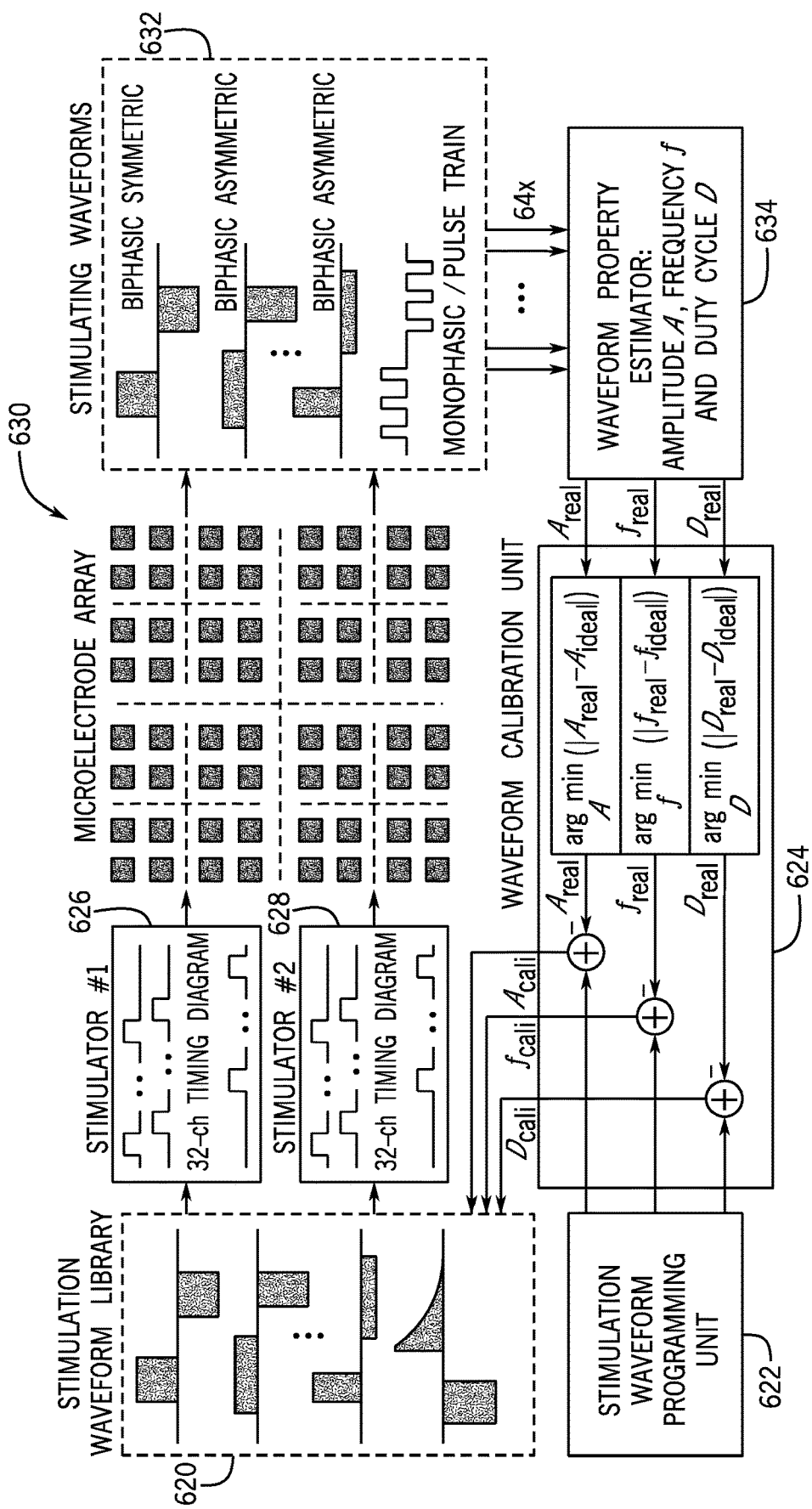
FIG. 6B is an operational flow chart setting forth one, non-limiting example of a process for operating the system of the present disclosure.

Referring to FIG. 6B, an operational diagram is provided to illustrate the functional capabilities of the above-described system. As shown in FIG. 6B, stimulation waveform library 620 may be maintain and/or a user may input a desired stimulation pattern and the timings for each electrode. The waveform library 620 may, for example, be stored within the on-chip memory 122. The above-described signal-processing systems operational present a stimulation waveform programming unit 622 and waveform calibration unit 624 that can be used to calculate the desired switching and mixing combination to match the simulation patterns selected or provided by a user to align the timing diagrams of the first and second stimulators 626, 628 relative to the microelectrode array 630 to yield stimulating waveforms 632. The selected stimulating waveforms 632 are processed to determine waveform properties by an estimator 634 that feeds back into the waveform calibration unit 624, thereby providing a control loop. Thus, the switching and mixing combination can be sent as a digital stream to control the stimulators described above.

As such, the controller 116 is configured to control the DCAN 408 to selectively electrically connect each of the pair of the current drivers 404, 406 to individual microelectrodes 208 in the array of microelectrodes to cause the desired electrical stimulation delivered to the subject to match a stored waveform.

The neural stimulators are designed to generate stimuli with a pulse-width from hundreds of microseconds to tens of milliseconds. Traditionally, thus the rising/falling of the stimulus pulse were not a focus of the designs and often not considered in operation. This is because of the physiology that it requires a ms-duration of cell membrane depolarization in order to activate neurons. Supplying fast rising/falling edges and fast pulses, requires a stronger driving capability than traditional systems that disregard these switching characteristics. By using one stimulator to simultaneously support multiple electrodes through high-speed interleaving, a high-speed driver, controller, operational protocol, and switching network are available, which can be used for high-speed rising/falling and, thereby, interleaving of pulses.

This is achieved, via a variety of design considerations. For example, as illustrated above, at the circuits level, the gates of all bias transistors in the current driver are driven by the output of an op-amp, which can provide very a fast settling time compared to a simple current mirror or cascode current mirror. Second, the current switching action is done by the above-described DCAN, which is designed for fast turning on/off for the output current. For example, as illustrated in FIG. 4, the current switching can be performed by controlling the gate voltage of the cascode transistors ($S_{C1}$, $S_{C2}$, $S_{A1}$, $S_{A2}$), thus having slower action.

Regarding charge balancing, due to non-ideal factors resulting from process variations, circuit parasitics, and electrode interface, there may be mismatch between anodic and cathodic pulses, causing a residual voltage to build up at the electrode interface. Prolonged charge accumulation could induce circuit malfunction and damage the electrode-tissue interface. To control the effect of residual voltage, the exemplary stimulator may have three charge-balancing schemes integrated therein, as described herein.

In a passive scheme, any of the stimulation electrodes 208 can be connected to the ground electrode 210 through a switch, $C_P$. In a foreground calibration scheme, the output from any of the drivers 204 can be routed to a calibration capacitor $C_c$ for foreground calibration. First, the output of the driver 204 is routed to the capacitor $C_c$ via the DCAN 408. Second, the capacitor is then connected to the RVM 128 via the DCAN 408 to sense the residual voltage $\Delta V_E$, which informs the mismatch between anodic and cathodic current. The value of the calibration sub-driver and pulse-width are then adjusted accordingly by the digital controller 116. Third, the capacitor $C_c$ is discharged to the GND. Another stimulus with updated parameters is generated and the process is repeated until the residual voltage is minimized. This design allows for calibrating each driver independent of each other and the stimulation electrode. The calibration can also be done during normal operation without affecting the stimulation pattern.

Figure 3:
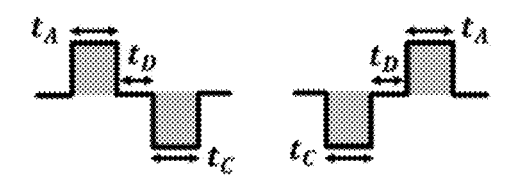
FIG. 3 is a timing diagram of stimulation waveforms and patterns used in operation of the systems and methods described herein.
Figure 3:
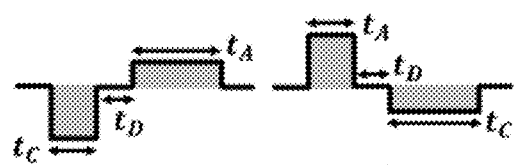
Figure 3:
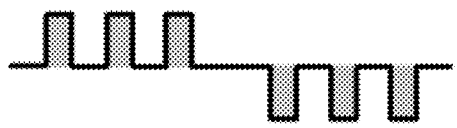

In a background charge-cancellation scheme, the stimulation electrode 208 can be connected to the residual voltage monitor 128 (not shown; part of the digital circuits 202) through a low-resolution SAR ADC 212 to monitor the residual electrode voltage $\Delta V_E$ after each stimulus. The digital circuits 202 then adjust stimulation parameters accordingly. The adjustable parameters include relative anodic/cathodic timing ($t_A$, $t_C$) and current ($S_{A0}$, $S_{C0}$). FIG. 3 shows examples of stimulation waveforms and patterns used in experiments (further discussed below). These charge balancing schemes allows the stimulator to perform self-calibration, which allows for the design to be compatible with different types of electrodes and a wide range of electrode size and impedance.

Traditionally, the programmability of stimulators was done by an off-chip controller, where all the operations of the designed stimulator, such as turning on the current, turning off the current, discharging the electrode, etc., are controlled by an off-chip FPGA (e.g. Intan stimulator). The controller constantly communicates with the stimulator through a high-speed data link. The drawback of this approach is that each stimulation pattern requires extra data transfer between the external controller and the stimulator. As a result, the pattern cannot be adjusted quickly and the bandwidth of the data link is a bottleneck for high channel count stimulator designs.

The stimulator chip 114 of the present disclosure has an on-chip digital controller 116 that can automatically generate the stimuli based on a pre-programmed set of parameters. With reference to FIG. 1B, any external controller (e.g. computing device 110) only needs to update individual parameters when necessary, thus greatly reducing the data transmission overhead and allowing for faster adapting of the stimulation pattern. Also, because the timing of the stimulus pulses is done on-chip, microsecond or, in some instances, nanosecond precision can be achieved.

Individual parameters can also be re-programmed independently in real-time by users, while the stimulus pattern can be generated via a customized single-wire communication protocol or the like. For example, using a 32-bit data frame at 1 Mbit/s, each parameter can be updated within 32 µs. The real-time programming capability of this stimulator can support closed-loop neuromodulation based on neural feedback.

Figure 7:
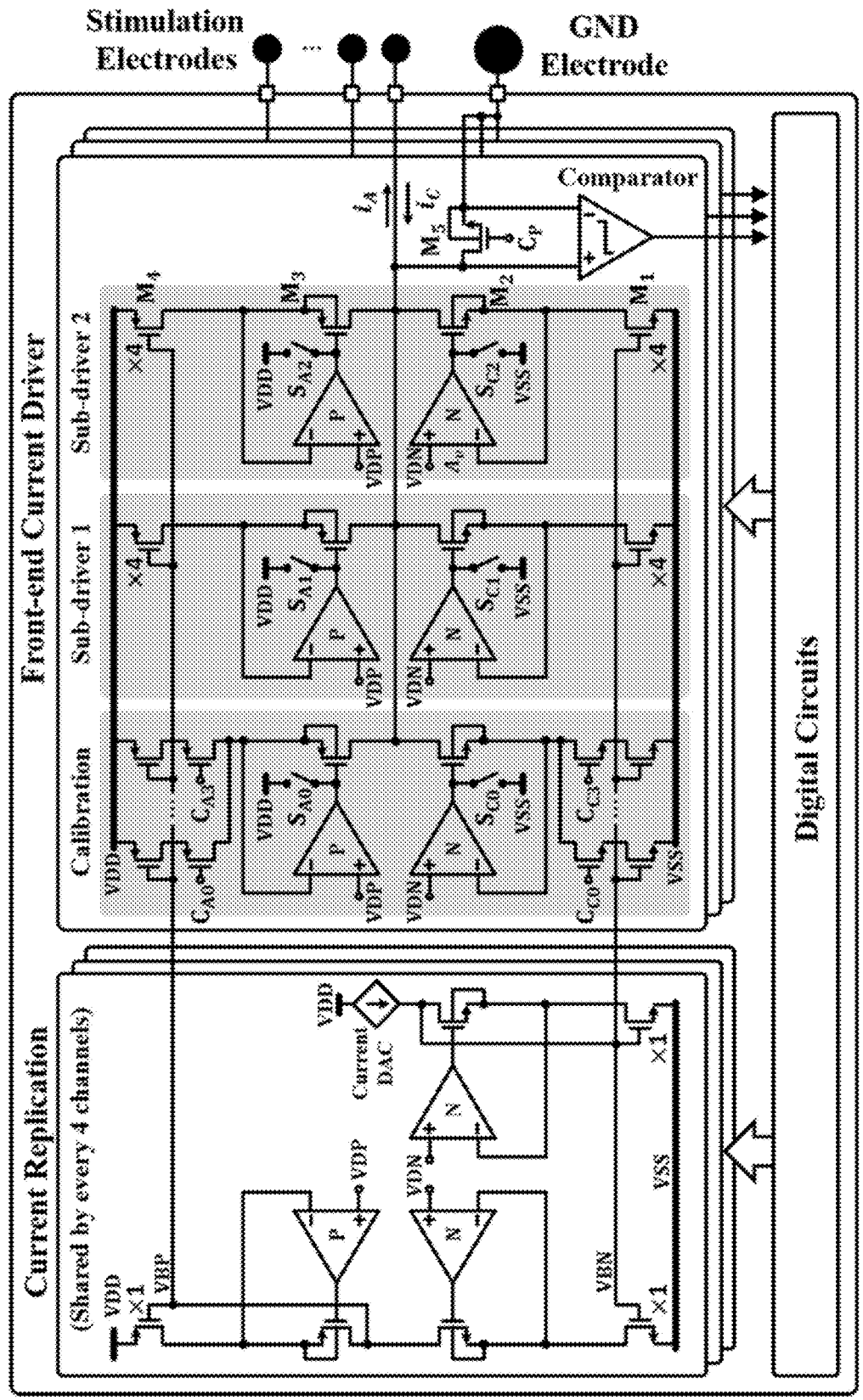
FIG. 7 is a circuit diagram that provides circuit schematics for a microstimulator for use in the systems of the present disclosure.

Referring now to FIG. 7, the schematic of another implementation of a microstimulator 800 in accordance with the present disclosure is shown. In the configuration shown, every four channels form a cluster that shares an 8-bit current-DAC and a current replication circuit, while each channel has independent anodic and cathodic current drivers. The drivers are designed based on a feedback-assisted current mirror structure to achieve high output impedance and voltage compliance.

To deliver both charge-balanced symmetrical and asymmetrical stimuli, each current driver can have two identical but independently programmable sub-drivers. There can also be included a third sub-driver with reduced width to length ratio (W/L) transistors for calibration. Overall, the stimulator's output current is modeled by:

$$I_{out}=I_{ref} \cdot x_D \cdot (4S_0+4S_1)+I_{cal}, \quad (1)$$

where $I_{ref}$ is the reference current, $x_D \in \{0, 1, \ldots, 255\}$ is the 8-bit current-DAC value, $S_0$, $S_1 \in \{0, 1\}$ are the sub-driver selectors, and $I_{cal}$ is the calibration current. With $I_{ref}$ configured to be about 0.5 µA in the low current mode and about 4 µA in the high current mode, such exemplary arrangements allow the stimulator to deliver a broad range of output current from, for example, 0.5 μA to 2 mA. The voltage compliance is related to bias voltages VDN and VDP, set at VSS+0.5V and VDD−0.5V respectively.

Regarding charge balancing, due to non-ideal factors resulting from process variations, circuit parasitics, and electrode interface, there may be mismatch between anodic and cathodic pulses, causing a residual voltage to build up at the electrode interface. Prolonged charge accumulation could induce circuit malfunction and damage the electrode-tissue interface. To lessen the effect of residual voltage, the exemplary stimulator may have both passive and active charge-balancing schemes integrated, as described above. Under the passive scheme, electrodes are shorted to the ground electrode through a transistor, M5. While this method can help avoid complex circuitry, a complete discharge could take relatively longer. The active charge-balancing refers to monitoring the residual voltage and adapting the subsequent stimuli via tuning of the current amplitude and pulse duration, which results in an alteration of net charge transfer. The current amplitude can be adjusted by the calibration sub-drivers $$I_{cal}=I_{ref} \cdot x_C \cdot k_C, \quad (2)$$

where $x_C \in \{0, 1, \ldots, 15\}$ is the 4-bit calibration value, and $k_C$ is a scaling factor. In various implementations, $k_C$ is approximately 0.05. The pulse duration is tuned by the internal clock generator with, for example, 1 μs precision. Active charge-balancing may be performed in the background without intervening with the normal operation.

Figure 8:
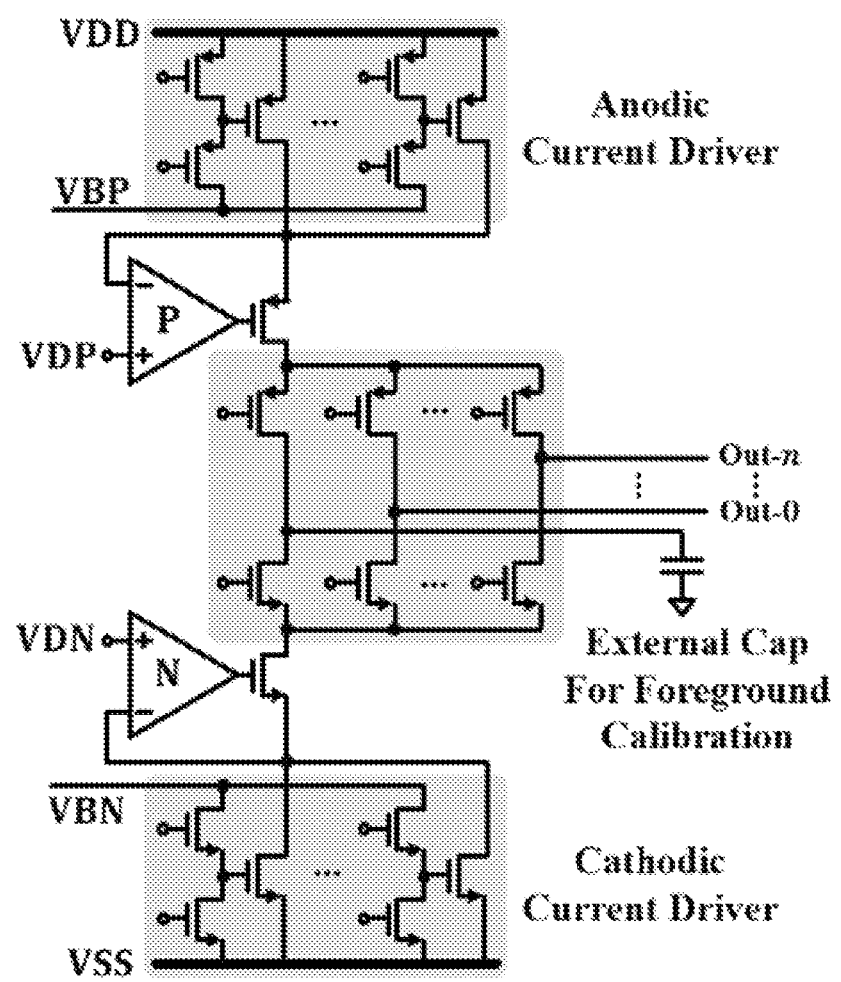
FIG. 8 is a circuit diagram that provides a further design for current drivers in a microstimulator chip for use in the systems of the present disclosure.

The alternative exemplary design of FIG. 8 includes one set of current drivers (anodic and cathodic) 902 supporting multiple non-concurrent outputs 904. An external capacitor $C_c$ allows foreground current calibration and can be shared among the entire stimulation channels.

Figure 9:
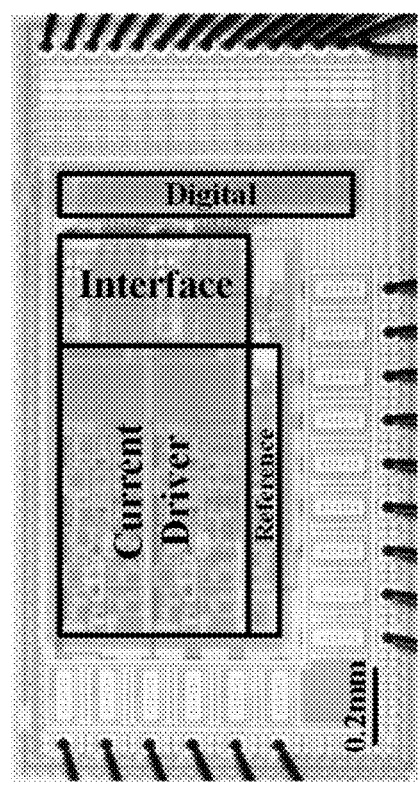
FIG. 9 is a layout diagram that provides a micrograph of an exemplary neurostimulator chip for use in the systems of the present disclosure.

Exemplary stimulator chips in accordance with any of the examples above can be designed and fabricated in a 0.18 μm high voltage (HV) CMOS process. FIG. 9 shows a possible chip micrograph. The front-end current drivers utilize high-voltage transistors, while the digital circuits adopt low-voltage transistors. Level shifters can be added at the interface between analog and digital circuits. Table 1 summarizes specifications of one, non-limiting version of the microstimulator.

TABLE 1

SPECIFICATIONS SUMMARY

| | |
|---|---|
| Technology | 0.18 μm HV CMOS |
| Stimulus Pattern | Biphasic/Monophasic/Pulse Train Symmetrical/Asymmetrical |
| Output Current | Low Current Mode: 0.5 μA-256 μA High Current Mode: 4 μA-2 mA |
| Pulse Width | 100 μs-4 ms (1 μs Increment) |
| Stimulation Rate | 0.1 Hz-200 Hz |
| Supply Voltage | 10/20 V |
| Charge-Balancing | Passive and Active |
| Output Impedance | >1TΩ at 10 μA >1GΩ at 1 mA |

Within this example, non-limiting implementation, the system can provide, for example, a 16-channel (or greater) stimulator integrated with a 16-channel (or greater) recorder on the same die. In certain configurations, a recorder and stimulator may be integrated on the same die, with simultaneous recording and stimulation using the same electrode. This is advantageous over many prior devices in which the stimulator and the recorder are connected to adjacent electrodes, as connecting the stimulator and recorder to the same electrode in such prior devices is expected to result in the stimulator increasing the noise of the recorder.

Regarding the digital controller and system operation, the stimulator may be programmed, in certain configurations, through a single-wire customized communication protocol. The controller may utilize (for example) a 32-bit data frame at 1 Mbit/s. The first 16-bit may encode the channel identification, while the second 16-bit may be the instruction set. In such configurations, the controller may support $2^{16}$ (65536) independent channels and $2^{16}$ (65536) distinct commands. Stimulation parameters may be loaded when the device is powered on. The stimulation waveforms and patterns can then be automatically generated by the internal clock generator. During the normal operation, individual parameters can be reprogrammed in real-time with (for example) 32 μs latency by sending appropriate commands.

Figure 10:
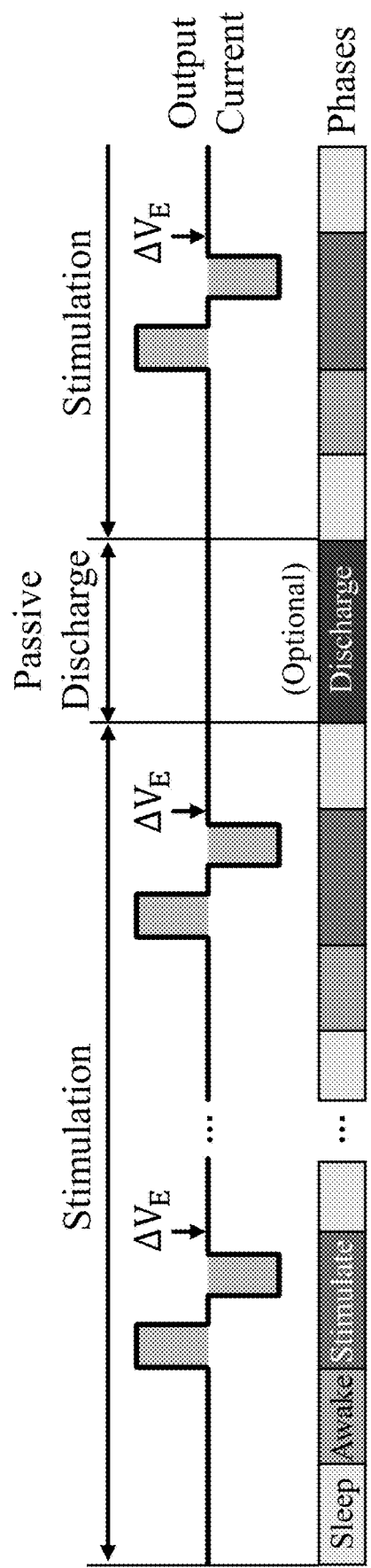
FIG. 10 is a timing diagram that provides an overview of one non-limiting example of system operation with sleep, awake, stimulate, and discharge stages.

In various configurations, the system operation of any of the microstimulation systems or chips described above can be divided into 4 stages: sleep, awake, stimulate, and optional discharge as illustrated in FIG. 10. During the sleep stage, the bias current of amplifiers and current-DACs may be turned off to reduce power consumption. The awake stage can be engaged (for example) at least 10 ms prior to the stimulus, where the bias current is turned on and stabilized. Next, the device can enter the stimulate stage and deliver stimuli through electrodes according to preprogrammed parameters. The residual voltage $V_{res}$ may be acquired after stimulation before the device goes back to sleep. After a number of cycles, the stimulator enters the optional discharge stage, where passive charge-balancing may be engaged.

Figures 11A, 11B:
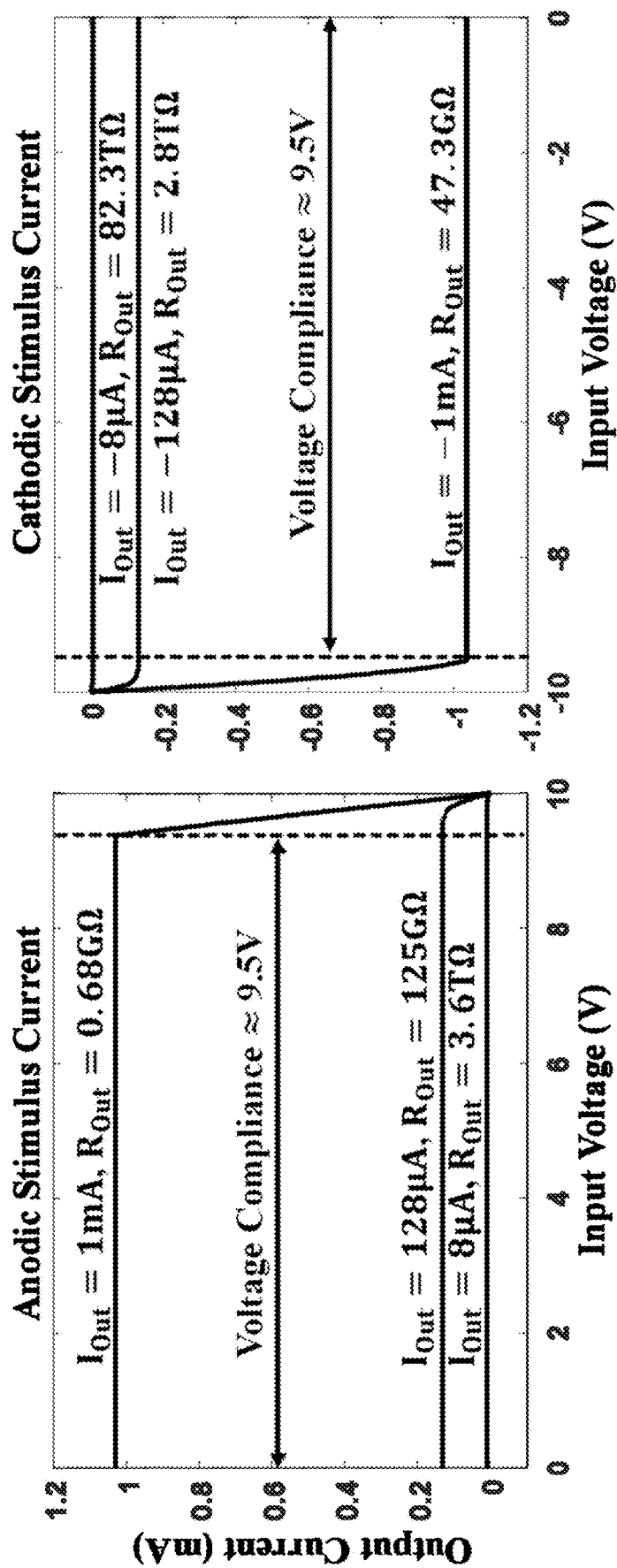
FIG. 11A is a graph that provides simulated anodic output current and anodic output impedance at multiple loading conditions for an exemplary stimulator with a high output impedance and high voltage compliance in accordance with the present disclosure.
FIG. 11B is a graph that provides simulated cathodic output current and cathodic output impedance at multiple loading conditions for an exemplar stimulator with a high output impedance and high voltage compliance in accordance with the present disclosure.

FIGS. 11A and 11B show a simulated output current and output impedance at multiple loading conditions. The output impedances are 0.68 GΩ@1 mA to 3.6 TΩ@8 μA for anodic and 47.3 GΩ@−1 mA to 82.3 TΩ@−8 μA for cathodic drivers, respectively. In various configurations, a voltage compliance of 19V (±9.5V) at 20V (±10V) power supply is achieved. High output impedance and voltage compliance help make residual voltage less dependent on electrode interface and pulse width duration.

Figure 12B:
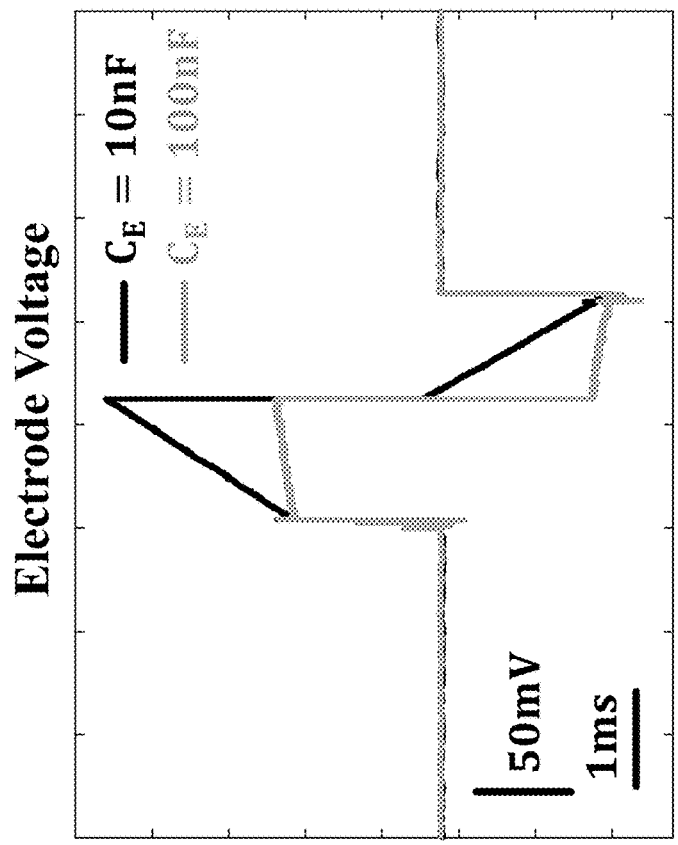
FIG. 12B is a graph that provides measured electrode voltage with different loading conditions corresponding with a simple electrode model in accordance with the present disclosure.
Figure 12A:
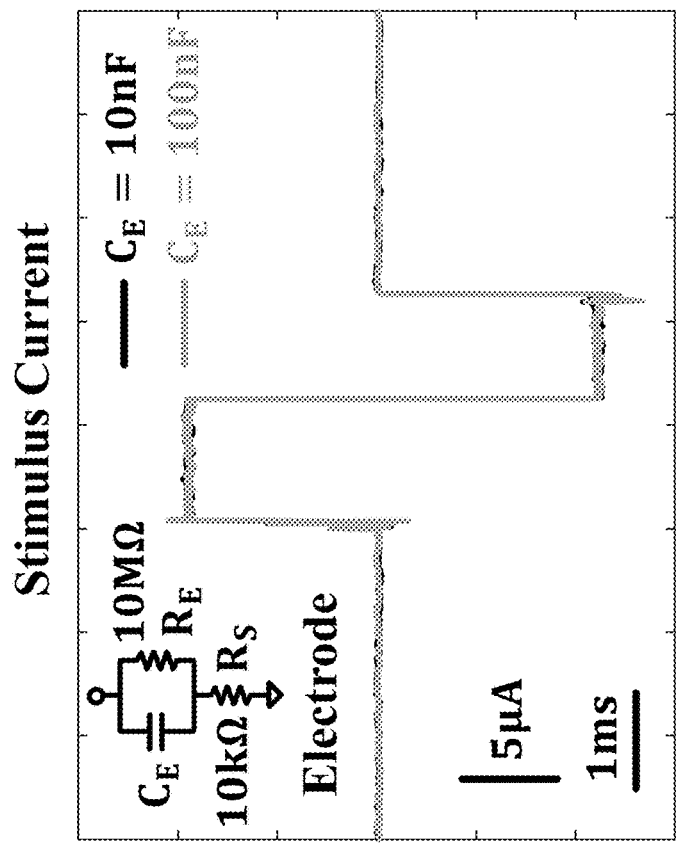
FIG. 12A is a graph that provides measured output current results corresponding with a simple electrode model in accordance with the present disclosure.
Figure 13:
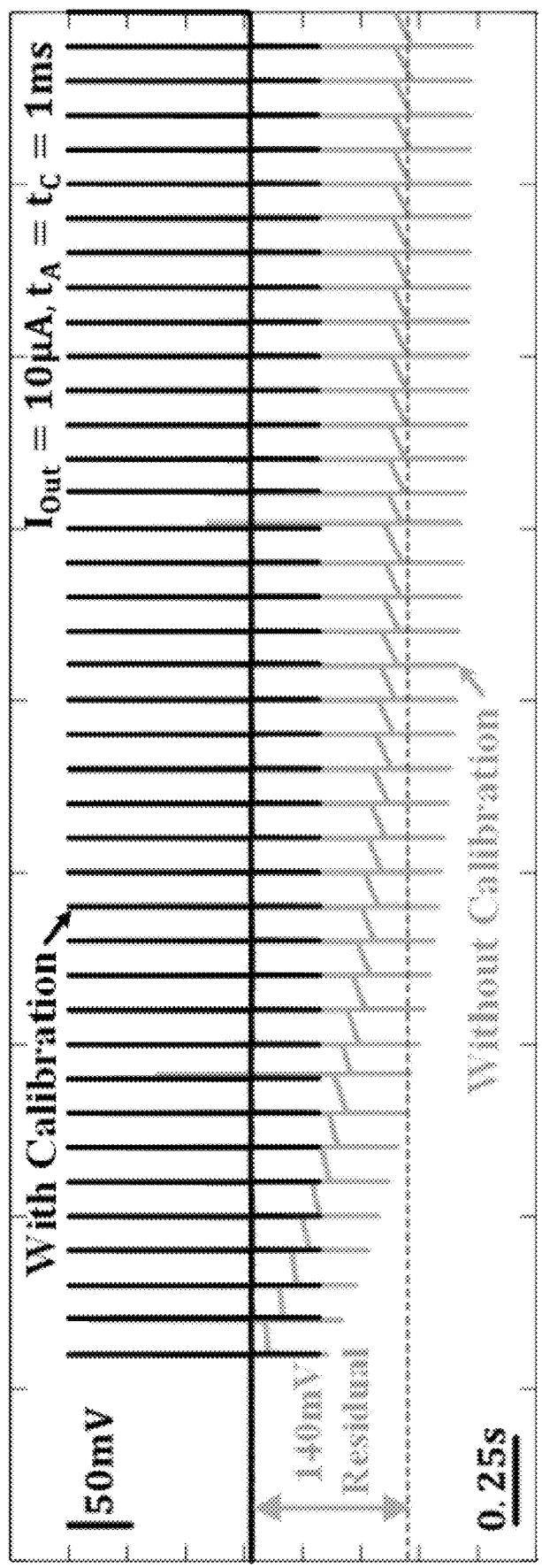
FIG. 13 is a graph that provides electrode voltage when supplied with a train of stimuli. Without active charge-balancing, a residual voltage greater than 140 mV builds up on the electrode interface. With active charge-balancing, the residual voltage is no longer observed.

For taking measurements using an exemplary version, the stimulator output may be connected to a simple electrode model (for example, $R_S=10$ kΩ, $R_E=10$ MΩ, and $C_E=10/100$ nF) to characterize its specifications. FIGS. 12A and 12B present the measured output current and electrode voltage when supplied with symmetrical biphasic pulses under different loading conditions. FIG. 13 shows electrode voltage with and without active charge-balancing. In these sessions, initially, there is residual voltage greater than 140 mV building up on the electrode interface after 5 seconds of stimulation. Under the active charge-balancing scheme, the residual voltage is no longer observed.

In vitro neural stimulation experiments have been conducted to demonstrate the function of exemplary stimulators. The experiments utilized cortical tissues extracted from E18 rat embryonic brain. The cell suspension was centrifuged and re-suspended in Neural Basal medium with supplements of B27, Pen-Strep, and L-glutamine. 30 μl of the cell suspension with a concentration of $4 \times 10^6$ cells/ml was transferred to the microelectrode array (MEA) dish (MultiChannel Systems). One day after plating, the culture medium was changed to a serum-free solution. During the experiments, the medium was replaced with Dulbecco's phosphate-buffered saline (DPBS).

Figure 14:
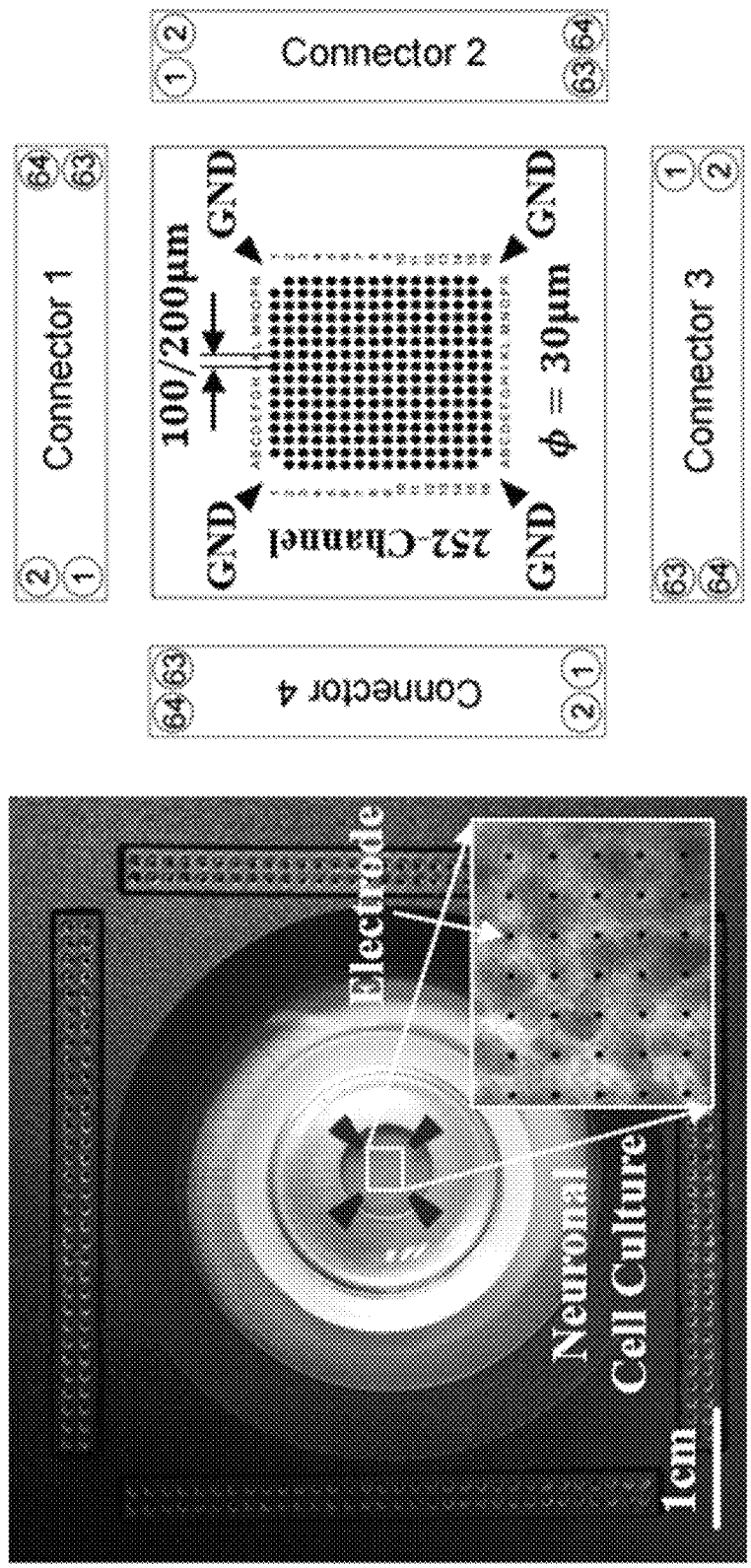
FIG. 14 is an image and corresponding connection diagram that illustrates microelectrode arrays (MEA) used in certain exemplary implementations in accordance with the present disclosure.
Figure 15:
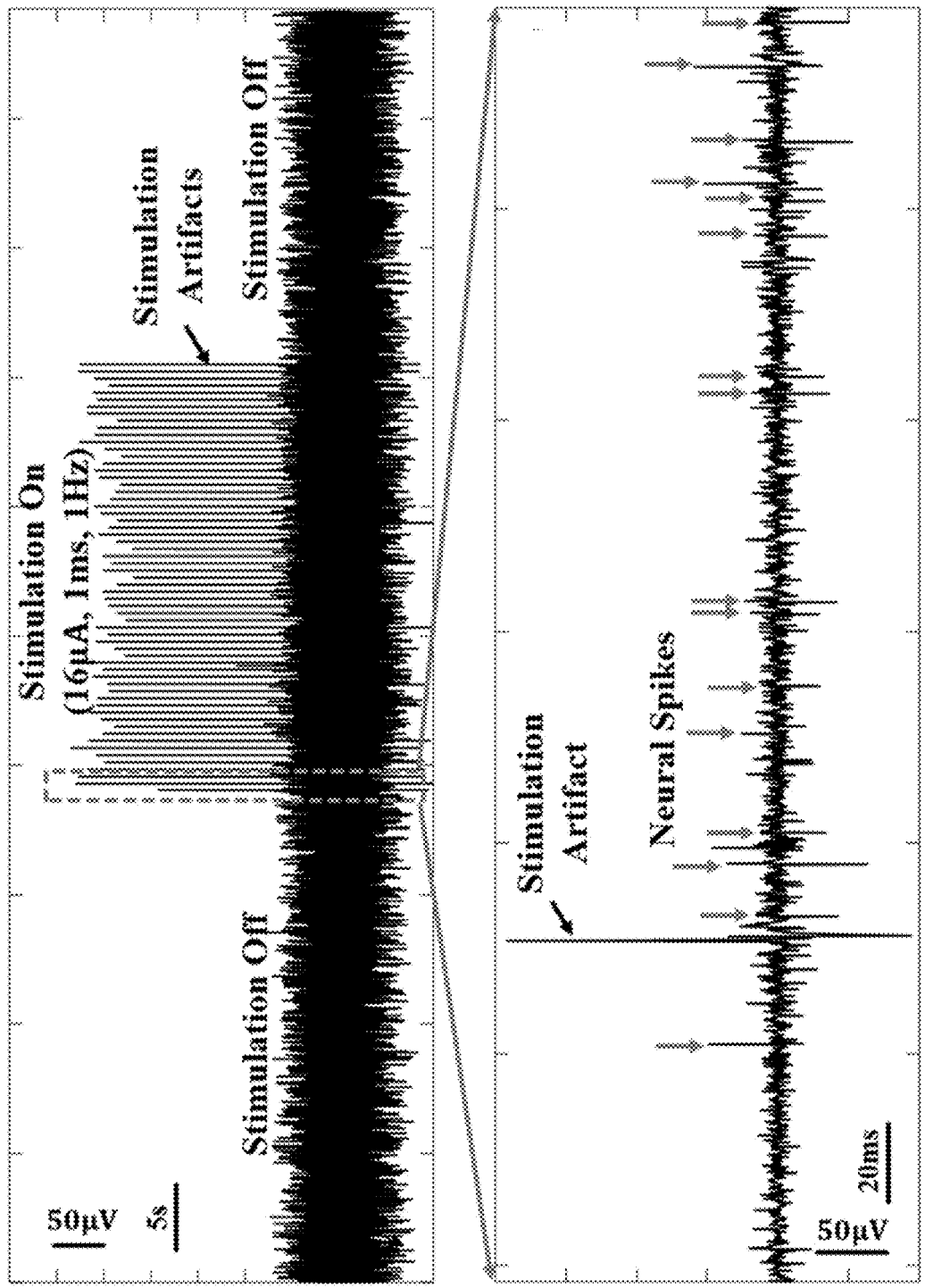
FIG. 15 is a graph that provides recorded neural signals under electrical microstimulation (top), and provides a zoom-in view showing a stimulation artifact and neural spikes superimposed in the same data sequence (bottom).
Figure 16B:
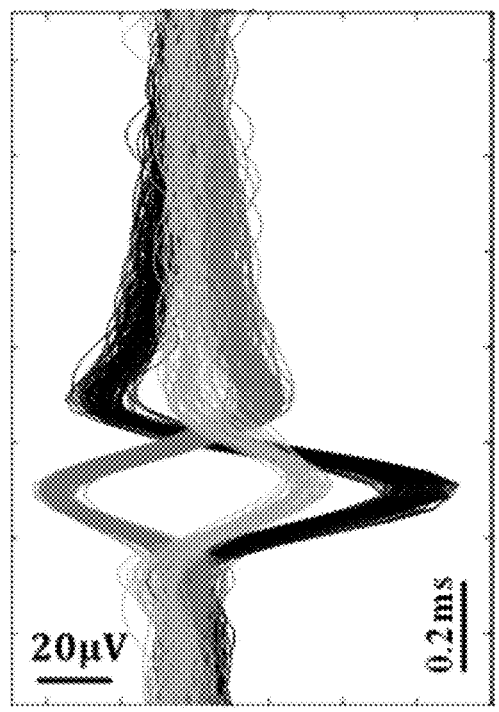
FIG. 16B is a graph that provides sorted spike clusters from an experimental operational session in accordance with the present disclosure.
Figure 16A:
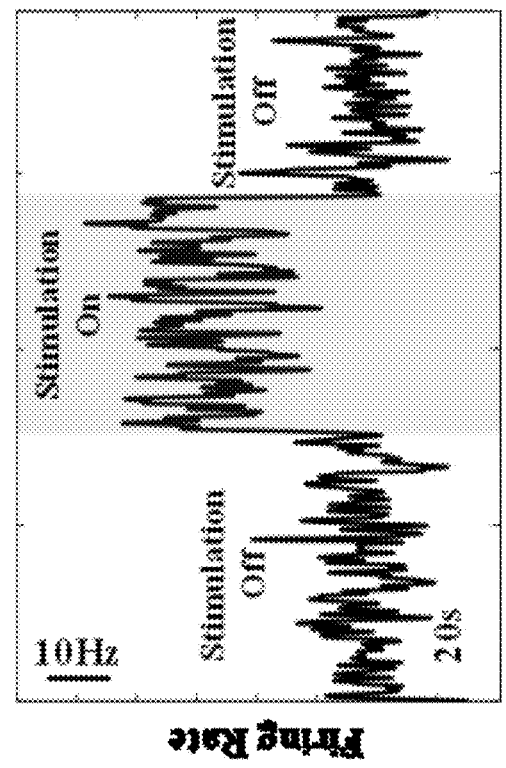
FIG. 16A is a graph that provides an estimated firing rate of a spike cluster in accordance with the present disclosure.
Figures 17A, 17B:
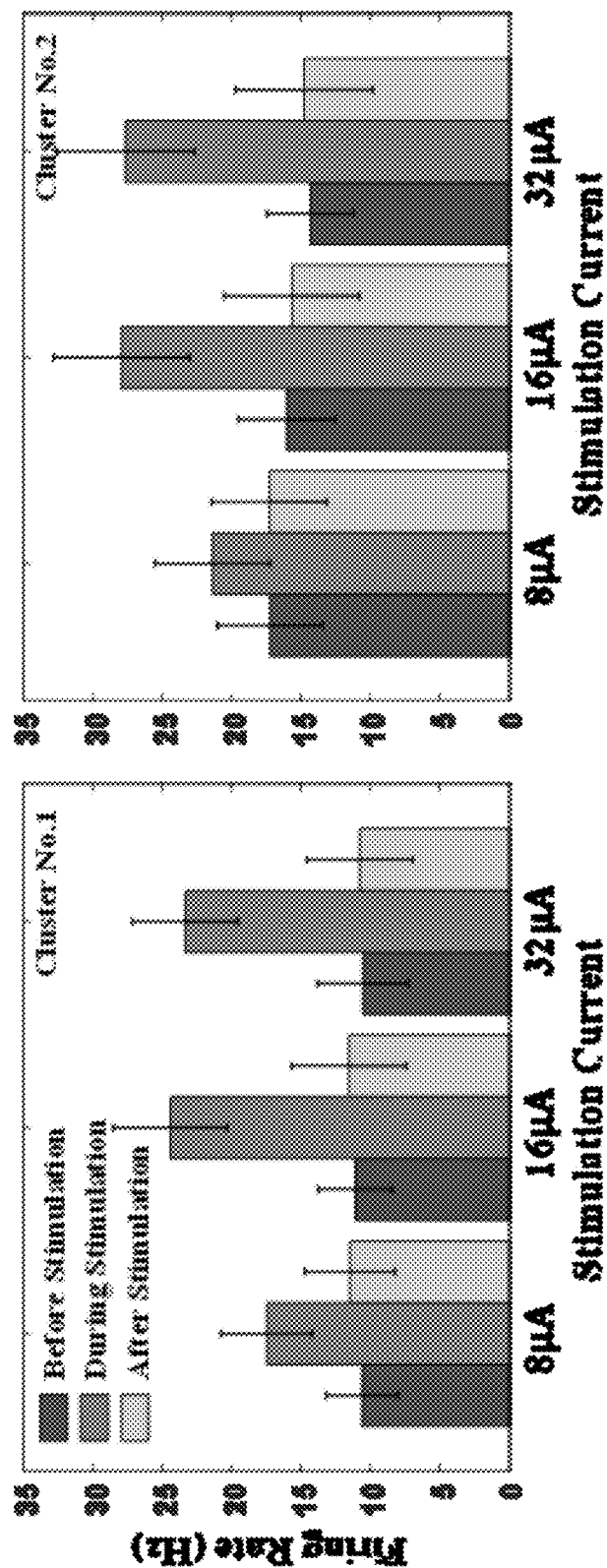
FIG. 17A is a graph that provides average firing rates of a first distinct cluster before, during, and after stimulation in accordance with the present disclosure.
FIG. 17B is a graph that provides average firing rates of a second distinct cluster before, during, and after stimulation in accordance with the present disclosure.

As shown in FIG. 14, the MEA dish has 252 high-impedance electrodes with 30 μm contact diameter, and 100/200 μm spacing. A small set of electrodes is selected for stimulation while adjacent electrodes are used for recording. In each experiment session, the stimulator was turned on for 60 seconds to deliver a train of symmetrical biphasic pulses. Different parameters were applied including current amplitude ranging from 2 µA to 64 µA, pulse width from 0.5 ms to 2 ms, and stimulation rate from 0.1 Hz to 10 Hz. The top of FIG. 15 shows an example of recorded neural signals including data sequences before, during, and after electrical microstimulation. The data obtained before and after stimulation are used as controlled baselines. Neural spikes are detected and classified using standard methods. The bottom of FIG. 15 is a zoomed-in view that shows a stimulation artifact and neural spikes superimposed in the same data sequence. FIG. 16B presents examples of spike clusters isolated from one experiment session while FIG. 16A plots the firing rate vs. time for one cluster. The firing rate can be seen increasing from 10 Hz (baseline) to 25 Hz when the stimulator is turned on, and going back to 10 Hz after the stimulator is turned off. FIGS. 17A and 17B show average firing rates of two spike clusters before, during, and after stimulation. The experiment has been repeated with different electrodes, stimulation parameters, and culture preparations, where the proposed stimulator can trigger and modulate the activity of neuronal cell culture.

Exemplary systems and methods thus provide a fully-integrated and flexible microstimulator that can support high voltage compliance and generate stimulation patterns with programmable waveform, timing, and amplitude. The stimulator has passive and active charge-balancing schemes integrated to reduce residual voltage and stimulation artifacts. Benchtop testing and in vitro experiment results have verified circuit specifications and validated system functionality, such as the triggering of neural spikes and modulation of neuronal firing rate.

The microstimulators discussed above can serve as a platform technology capable of supporting a wide range of neuroscience applications that involve (acute) electrical microstimulation. Examples include such applications as cortical stimulation, deep brain stimulation (DBS), and vagus nerve stimulation, among others. Exemplary systems and methods can be used to materialize neural stimulation instruments that provide superior performance and functionality compared to current devices.

Moreover, in part due to its high-density, the exemplary designs can be integrated into large-scale, miniaturized biomedical implants that could be applied to many neuromodulation applications, such as neuroprosthetics to restore motor and sensory function (e.g., neuromuscular stimulation, retinal prosthesis, peripheral nerve stimulation, etc.), neurorepair to aid rehabilitation from brain injuries (e.g., deep brain stimulation), and neurotherapeutics to treat nervous system disorders (e.g., epilepsy, Alzheimer's disease, Parkinson's disease, etc.).

The present invention has been described in terms of one or more preferred versions, and it should be appreciated that many equivalents, alternatives, variations, additions, and modifications, aside from those expressly stated, and apart from combining the different features of the foregoing versions in varying ways, can be made and are within the scope of the invention. The true scope of the invention will be defined by the claims included in any later-filed utility patent application claiming priority from this provisional patent application.

We claim:

1. An implantable neurostimulator system comprising:
   an array of microelectrodes configured to deliver a desired electrical stimulation to a subject;
   a pair of current drivers electrically coupled to each microelectrode in the microelectrode array, wherein each current driver in the pair of current drivers is configured to deliver a respective portion of an electrical signal to the array of microelectrodes whereby the respective portions, together, form the electrical signal delivered to the array of microelectrodes to deliver the desired electrical stimulation through the array of microelectrodes to the subject;
   a dynamic current allocation network (DCAN) coupled to the pair of current drivers and the array of microelectrodes to selectively electrically connect each of the pair of the current drivers to individual microelectrodes in the array of microelectrodes to deliver the electrical signal to selective collections of less than all microelectrodes in the array of microelectrodes to deliver the desired electrical stimulation; and
   wherein the pair of current drivers and the DCAN are arranged in respective or a common housing configured to be implanted into the subject.

2. The system of claim 1 further comprising a controller configured to control the DCAN to selectively electrically connect each of the pair of the current drivers to individual microelectrodes in the array of microelectrodes to cause the desired electrical stimulation delivered to the subject to match a stored waveform.

3. The system of claim 2 wherein the stored waveform is stored in a memory accessible by the controller and rewritable to receive a user-selected waveform.

4. The system of claim 1 wherein the stored waveform has one of a symmetrical biphasic form, an asymmetrical biphasic form, or a pulse train form.

5. The system of claim 1 wherein the controller is configured to control the DCAN to selectively electrically connect each of the pair of the current drivers to individual microelectrodes in the array of microelectrodes to connect one current driver to multiple microelectrodes or couple the pair of current drivers to one microelectrode.

6. The system of claim 1 wherein an output of one or both of the current drivers in the pair of current drives is coupled to an output configured to receive a calibration capacitor.

7. The system of claim 6 wherein the DCAN is configured to couple the pair of current drivers to the calibration capacitor to calibrate each current driver independent of each other and the microelectrodes.

8. The system of claim 1 wherein DCAN is configured to electrically connect a given microelectrode to a residual voltage monitor (RVM) to sense a residual voltage on the given microelectrode upon delivering desired electrical stimulation and further comprising a controller configured to adjust parameters of the electrical signal to reduce the residual voltage.

9. The system of claim 1 wherein the controller is configured to adjust parameters of the electrical signal to reduce the residual voltage upon each delivery of the desired electrical stimulation.

10. The system of claim 1 wherein the DCAN is configured to electrically connect the pair of current drivers and the array of microelectrodes to deliver the desired electrical stimulation to have rising or falling edges of less than 1 µs or a stimulation rate of 300 kHz.

11. The system of claim 1 wherein the pair of current drivers include an anodic driver and a cathodic driver.

12. An implantable neurostimulator system comprising:
   an array of microelectrodes configured to deliver a desired electrical stimulation to a subject;

a pair of current drivers electrically coupled to each microelectrode in the microelectrode array, wherein each current driver in the pair of current drivers is configured to deliver a respective portion of an electrical signal to the array of microelectrodes whereby the respective portions, together, form the electrical signal delivered to the array of microelectrodes to deliver the desired electrical stimulation through the array of microelectrodes to the subject;

a dynamic current allocation network (DCAN) coupled to the pair of current drivers and the array of microelectrodes to selectively electrically connect each of the pair of the current drivers to individual microelectrodes in the array of microelectrodes to deliver the electrical signal to selective collections of less than all microelectrodes in the array of microelectrodes to deliver the desired electrical stimulation; and a controller configured to control the DCAN to selectively electrically connect each of the pair of the current drivers to individual microelectrodes in the array of microelectrodes to cause the desired electrical stimulation delivered to the subject to match a stored waveform.

13. The system of claim 12 wherein the stored waveform is stored in a memory accessible by the controller and rewritable to receive a user-selected waveform.

14. The system of claim 12 wherein the stored waveform has one of a symmetrical biphasic form, an asymmetrical biphasic form, or a pulse train form.

15. The system of claim 12 wherein the controller is configured to control the DCAN to selectively electrically connect each of the pair of the current drivers to individual microelectrodes in the array of microelectrodes to connect one current driver to multiple microelectrodes or couple the pair of current drivers to one microelectrode.

16. The system of claim 12 further comprising at least one housing configured to at least partially surround one of the array of microelectrodes, the pair of current drivers, the DCAN, or the controller to implant the neurostimulator system within the subject.

17. The system of claim 12 wherein an output of one or both of the current drivers in the pair of current drives is coupled to an output configured to receive a calibration capacitor.

18. The system of claim 17 wherein the DCAN is configured to couple the pair of current drivers to the calibration capacitor to calibrate each current driver independent of each other and the microelectrodes.

19. The system of claim 14 wherein DCAN is configured to electrically connect a given microelectrode to a residual voltage monitor (RVM) to sense a residual voltage on the given microelectrode upon delivering desired electrical stimulation and further comprising a controller configured to adjust parameters of the electrical signal to reduce the residual voltage.

20. The system of claim 12 wherein the DCAN is configured to electrically connect the pair of current drivers and the array of microelectrodes to deliver the desired electrical stimulation to have rising or falling edges of less than 1 µs or a stimulation rate of 300 kHz.

* * * * *